United States Patent
Abae

[11] Patent Number: 5,993,461
[45] Date of Patent: Nov. 30, 1999

[54] LAPAROSCOPIC INSTRUMENT FOR MANIPULATING THE UTERUS DURING LAPAROSCOPIC SURGERY

[76] Inventor: Mick Abae, 1271 NW. 100th Way, Plantation, Fla. 33322

[21] Appl. No.: 09/003,843

[22] Filed: Jan. 7, 1998

[51] Int. Cl.⁶ .................................................. A61B 17/00
[52] U.S. Cl. .......................................................... 606/119
[58] Field of Search ...................... 606/119, 120, 606/205–209, 191–193, 198; 604/55; 600/204, 205

[56] References Cited

U.S. PATENT DOCUMENTS

| | | |
|---|---|---|
| 2,113,246 | 4/1938 | Wappler . |
| 4,430,076 | 2/1984 | Harris . |
| 4,763,669 | 8/1988 | Jaeger . |
| 4,880,015 | 11/1989 | Nierman . |
| 5,108,413 | 4/1992 | Moyers . |
| 5,195,964 | 3/1993 | Kletzky et al. . |
| 5,217,466 | 6/1993 | Hasson . |
| 5,362,294 | 11/1994 | Seitzinger . |
| 5,370,134 | 12/1994 | Chin et al. . |
| 5,382,252 | 1/1995 | Failla et al. . |
| 5,394,863 | 3/1995 | Sanford et al. . |
| 5,417,684 | 5/1995 | Jackson et al. . |
| 5,431,662 | 7/1995 | Nicholas . |
| 5,474,057 | 12/1995 | Makower et al. . |
| 5,490,819 | 2/1996 | Nicholas et al. . |
| 5,571,115 | 11/1996 | Nicholas . |
| 5,578,048 | 11/1996 | Pasqualucci et al. . |

*Primary Examiner*—Michael Buiz
*Assistant Examiner*—Vikki Trinh
*Attorney, Agent, or Firm*—Malin, Haley & DiMaggio, P.A.

[57] ABSTRACT

A laparoscopic instrument for manipulating an internal organ during surgery comprising an elongated cannula and a plurality of elongated, individually movable finger prongs operatively associated with the cannula, for engaging and manipulating an internal organ. The finger prong elements are incrementally movable from an open configuration wherein the finger prong elements are substantially spaced, to a closed configuration wherein the finger prong elements are substantially adjacent. A handle is connected to the proximal end of the cannula and includes a finger prong actuating lever for allowing the user to open and close the finger prong elements.

7 Claims, 6 Drawing Sheets

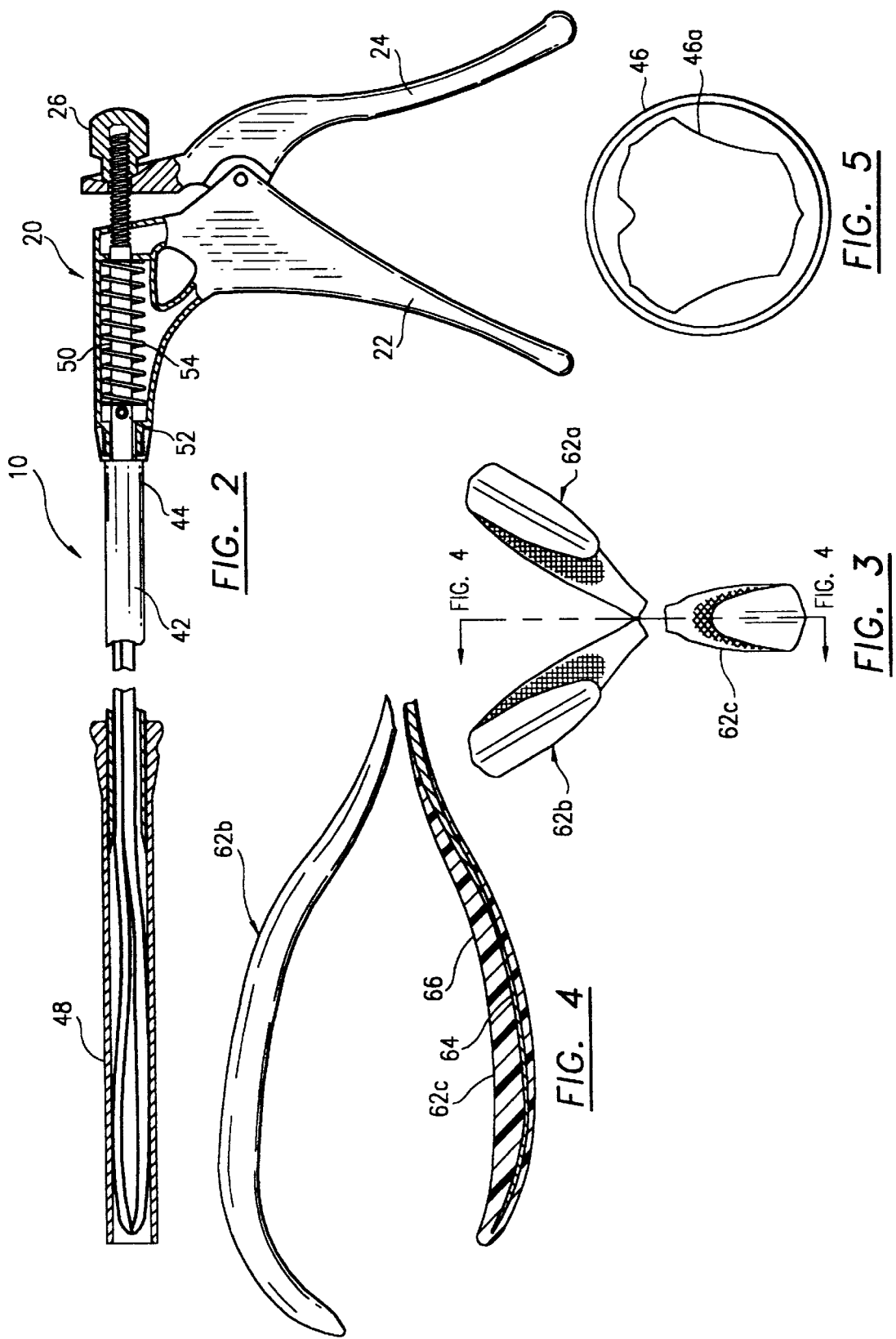

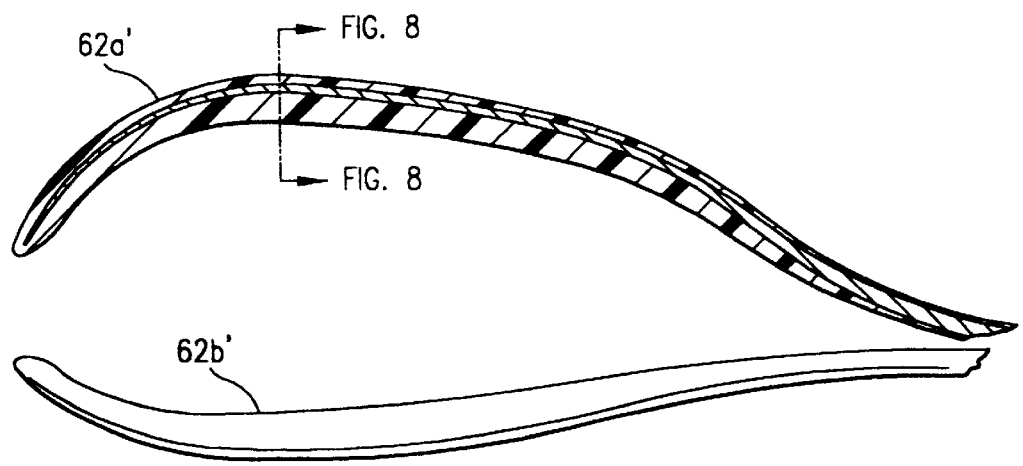
FIG. 7
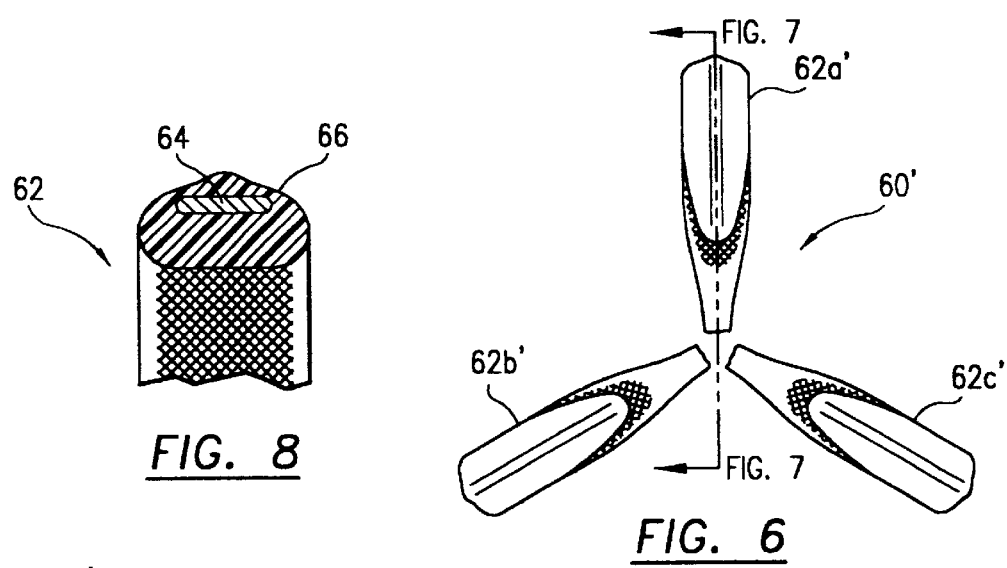
FIG. 8
FIG. 6
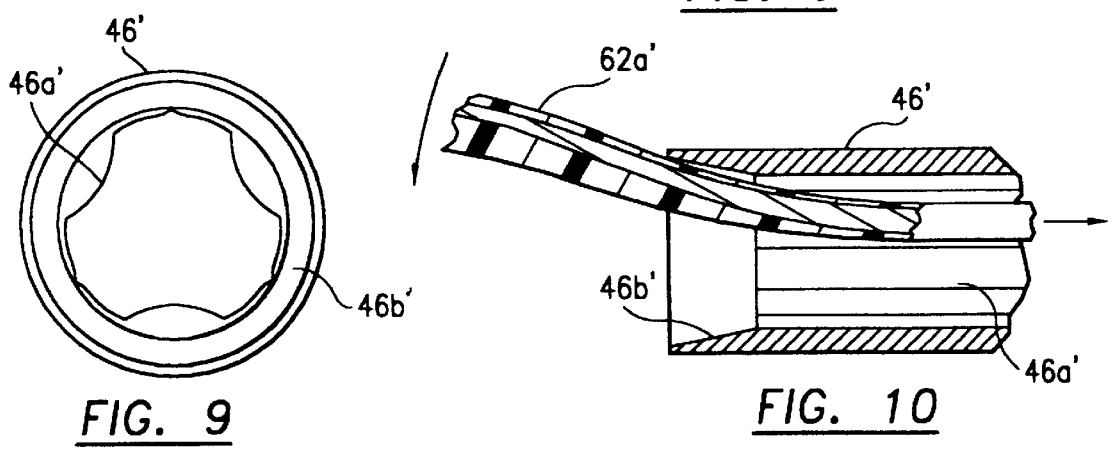
FIG. 9
FIG. 10

LAPAROSCOPIC INSTRUMENT FOR MANIPULATING THE UTERUS DURING LAPAROSCOPIC SURGERY

BACKGROUND OF THE INVENTION

1. Field of the Invention

This invention relates to surgical instruments for internal surgical use during laparoscopic surgery, and specifically to a laparoscopic surgical instrument that allows the surgeon to accurately provide manipulative movement of an internal organ, such as the uterus, while performing laparoscopic surgery or treatment on a patient.

2. Description of the Background Art

In recent years, laparoscopic examination and surgery has become one of the foremost procedures for improving internal organ surgery, resulting in improved, minimally invasive, techniques, less trauma to the patient during surgery, and much quicker recovery times after surgery.

Laparoscopic examination and surgery involves the insertion of a rigid tube in a small incision in the patient, the tube being called a trocar, which itself becomes the passageway for insertion of a cannula which includes one or more specialized instruments and/or visual examining devices. Thus, the introduction of various devices into the patient's body is facilitated by inserting an instrument containing cannula into a tubular trocar conduit that has been inserted into the patient's body. A number of instruments are known in the field of laparoscopic surgery; for example, visual examining devices, such as a TV camera, and also specific surgical tools, such as scissors and cauterizing devices, may be inserted into the patient for performing specific surgical procedures on various internal organs.

In certain laparoscopic procedures three cannulas are introduced into the patient through trocar conduits. A first cannula is typically used for visual examination, and allows the surgeon to view the inside organs of the patient, typically on a TV monitor. A second cannula would be used to introduce the actual surgical device, such as scissors or cauterizing device, as required. A third cannula may be utilized for additional surgical instruments necessary in performing the specific operation, or for introducing or draining fluid.

With respect to treatment of the uterus in surgical operations, it is often necessary or desirable for the surgeon to be able to move or manipulate portions of the uterus during the operation. Present day techniques involve the use of inserting instruments through the vagina and cervix into the uterus, such that the uterus is moved from within. This may require an extra person on the surgical team.

U.S. Pat. No. 4,430,076, issued Feb. 7, 1984 to Harris, shows a combined uterine injector and manipulative device, which includes an inflatable member at the insertable end that is inserted into the uterus. The device is secured in the uterus and enables the surgeon to manually position the uterus for examination purposes.

U.S. Pat. No. 5,362,294, issued Nov. 8, 1994 to Seitzinger, shows the use of a sling for positioning an internal organ during laparoscopic surgery. This is an elongated web having sutures on each end that actually allows the surgeon to manipulate an organ, such as the uterus, inside the patient, from outside the patient by pulling on the sutures. The apparatus disclosed by Seitzinger requires at least an additional person in the operating room to manipulate the sutures while the surgeon operates on the patient.

U.S. Pat. No. 5,217,466, issued Jun. 8, 1993 to Hasson, discloses a guide for facilitating the performance of internal surgery, such as laparoscopic surgery, which has a rotatable guide member that can be positioned within specific directions within an organ, such as the uterus. Hasson discloses an end tip which is curvable through manipulating manual devices, and the device provides for access through the uterine cavity to the fallopian tubes for purposes of intratubal insemination.

U.S. Pat. No. 5,431,662, issued Jul. 11, 1995 to Nicholas, shows a manually activated manipulator apparatus for manipulating a uterus for examination of the uterine cavity during a surgical procedure. While the manipulator apparatus shown is useful for laparoscopic surgery in procedures involving the uterus, the device is still introduced through the vagina and requires manipulation from within the uterus, through the use of the apparatus.

U.S. Pat. No. 5,464,409, issued Nov. 7, 1995 to Mohajer, shows a uterine manipulator and protector that again provides for manipulation of the uterus from within.

U.S. Pat. No. 5,237,985, issued Aug. 24, 1993 to Hodgson et al., shows a uterine retractor that accesses the uterus through the vaginal tract.

U.S. Pat. No. 5,571,115, issued Nov. 5, 1996 to Nicholas, provides for a manipulator apparatus that again is used to access the uterus through the vaginal tract from within.

U.S. Pat. No. 5,417,684, issued May 23, 1995 to Jackson et al., shows a laparoscopic surgical grasper with a loop with gripping formations. The loop is useful for holding and manipulating body organs and body tissue.

U.S. Pat. No. 5,490,819, issued Feb. 13, 1996 to Nicholas et al., shows an articulating endoscopic surgical apparatus. This device shows an endoscopic tool that includes a cooperating jaw.

None of the devices in the prior art show an effective laparoscopic tool that would allow the surgeon to manipulate the uterus by engagement of the exterior uterine wall during laparoscopic surgery. The invention may also be constructed in different sizes to be used on other organs such as an ovary, gall bladder or the like.

SUMMARY OF THE INVENTION

The surgical tool in accordance with the present invention includes a rigid handle housing that has a first handle, that receives one or more fingers and is shaped to be grasped by a physician, rigidly attached thereto. A second, movable handle is pivotally attached to the handle housing and may be spring biased to hold the second or movable handle in a predetermined position, thereby separating the first handle from the second handle. The spring allows the physician to squeeze the handles together against a spring biasing force to perform the gripping action as described herein.

The operative shaft of the invention is an elongated cannula that is rigidly attached to the handle housing at the proximal end and has a prong actuating housing at the distal end. A rigid actuating shaft is connected from the movable handle to a linkage mechanism contained in the prong actuating housing. The cannula is sized for insertion into a patient's body through a trocar conduit. The invention may further include a slidable sleeve axially disposed around the cannula for reasons that will soon become apparent.

At the distal end of the device, three or four elongated, finger-like prongs or digits are pivotally connected to the center actuating shaft through the prong actuating housing. The manipulating finger prongs are biased, or spring-loaded, through the handle spring to a full open position. The manipulating finger prongs are spaced approximately 60° apart, and the end tips of the fingers can be brought together by squeezing on the handle against the spring biasing force. When the movable handle is released away from the rigid handle, the finger prongs, by movement of the central shaft and the linkage, achieve an outwardly open position, the diameter of which is the approximate cross sectional diameter of the uterus.

Each finger prong is an elongated, semi-rigid member, arcuately curved to emulate a slightly curved human finger with a smoothed end portion that would not rupture or puncture the uterus wall when in contact therewith.

A physician can, by squeezing the handles together, cause the rigid finger prongs to move pivotally in a direction towards a center portion relative to each other, which would result in a grasping action, for example, on the outer uterus wall. The spring tension assembly facilitates feedback to the user and allows the amount of torque or force placed on the uterine wall to be sensed by variation in grasping resistance. Once the uterus has been grasped by the surgeon with the three (or four) finger prongs, the surgeon can move the uterus forward or backward, that is longitudinally along the shaft of the tool, away or toward the surgeon, and can also cause the uterus to be rotated by rotating the device once the outer uterine wall has been grasped.

During a laparoscopic surgical procedure, either on or involving the uterus, where it is required to manipulate the uterus, the grasping tool cannula of the present invention would be inserted through one of three or more trocars normally inserted into the patient during laparoscopic surgery. Thus, the surgeon, while watching the internal organs of the patient, can go from one trocar to another when it is required to adjust the position of the uterus, while at the same time using another tool to perform the surgical procedure. By using the present grasping tool invention, the surgeon can easily and quickly move or position the uterus as required to perform the surgical operation.

It is an object of this invention to provide an improved laparoscopic tool for laparoscopic surgery that allows the surgeon to manually and safely grasp and manipulate the uterus laparoscopically from outside the uterus.

Another object of this invention is to provide an improved laparoscopic tool that can be readily inserted through a cannula into a patient for laparoscopic manipulation of the uterus, eliminating the need for inter-vaginal manipulation of the uterus during surgery.

And yet another object of the present invention is to provide an improved laparoscopic tool that can easily grasp the uterus from the outside for manipulation during surgery without causing trauma to the uterus.

Still another object of the present invention is to provide an improved laparoscopic tool that can be readily inserted through a cannula into a patient for laparoscopic manipulation of the uterus by grasping of the outer uterine wall.

In accordance with these and other objects which will become apparent hereinafter, the instant invention will now be described with particular reference to the accompanying drawings.

BRIEF DESCRIPTION OF THE DRAWINGS

FIG. 2 is a side elevational view, in partial section, of the embodiment of FIG. 1;

FIG. 3 is a front elevational view depicting a three finger prong embodiment;

FIG. 4 is a partial side elevational view along section line 4—4 of FIG. 3;

FIG. 5 is an end view of the prong actuating housing portion of the elongated cannula for the three finger prong embodiment depicted in FIGS. 3 and 4;

FIG. 6 is a front elevational view depicting the finger prongs of an alternate three finger prong embodiment;

FIG. 7 is a partial side elevational view along section line 7—7;

FIG. 8 is a front sectional view of a finger prong along section line 8—8 in FIG. 7;

FIG. 9 is an end elevational view of the prong actuating housing portion of the elongated cannula of for the three prong embodiment depicted in FIGS. 6 through 8;

FIG. 10 is a fragmentary side elevational view of the prong actuating housing portion of the elongated cannula of the invention, in partial section;

DESCRIPTION OF THE PREFERRED EMBODIMENTS

Figure 1:
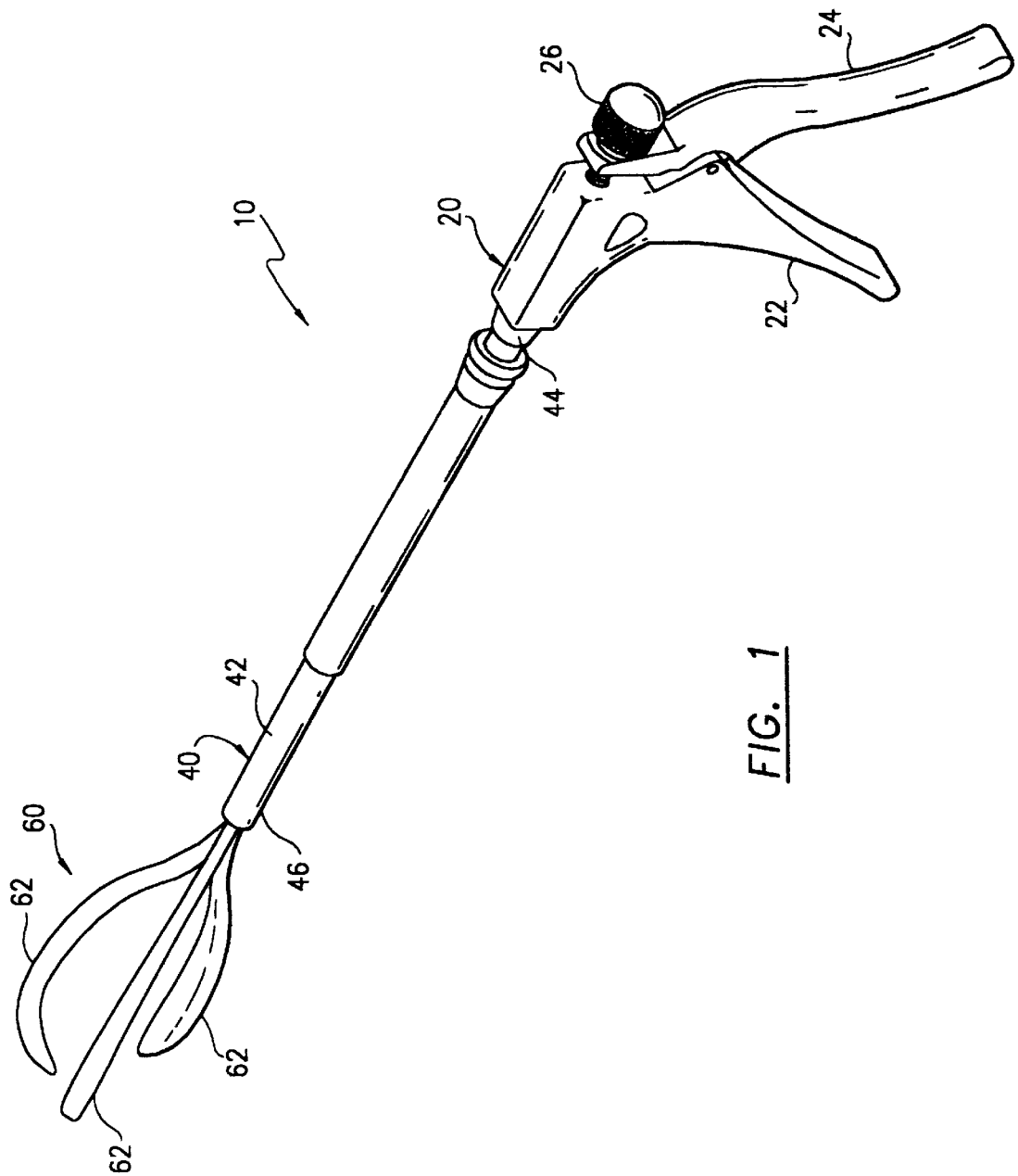
FIG. 1 is a top rear perspective view of a preferred three finger prong, embodiment of the present invention.

With reference to FIGS. 1 and 2, there is depicted a surgical tool in accordance with the present invention, generally referenced as 10. Surgical tool 10 includes a rigid handle housing, generally referenced as 20, which includes a first handle 22 rigidly attached to housing 20, and a second movable handle or lever 24 pivotally attached to housing 20. Surgical tool 10 further includes an operative shaft assembly, generally referenced as 40, which includes an elongated cannula 42 that is rigidly attached to the handle housing at its proximal end 44 and which further includes a prong actuating portion incorporated at its distal end 46. Cannula 42 is preferably sized for insertion into a patient's body through a conventionally sized trocar.

As best depicted in FIG. 2 a rigid actuating shaft 50 is connected at one end to movable handle 24 and connected at its opposite end to a finger prong assembly, generally referenced as 60, by a linkage mechanism 52. Movable handle 24 is pivotally connected to handle housing 20 and further connected to a threaded end portion of shaft 50 by internally threaded connector 26. Helical spring 54 is disposed within handle housing 20 and biases shaft 50 toward an extended position. As is apparent, actuating movable handle 24 results in compression of spring 54 and the retraction of shaft 50 and finger prong assembly 60 relative to the distal end 46 of cannula 42. The invention further includes a slidable sleeve 48 axially disposed about cannula 42 for reasons further discussed herein below.

As best depicted in FIGS. 3–5, a finger prong assembly 60 includes a plurality of resiliently flexible, yet semi-rigid, finger prong elements 62a–c. In the preferred embodiment each finger prong element 62a–c includes a resilient spine 64 surrounded by protective outer coating 66. Spine elements 64 may be made of any suitable resilient material, such as surgical grade spring steel. FIG. 8 shows a cross-sectional view of one structure of a preferred embodiment of a finger prong element 62, having a protective outer coating 66 and spine 64.

The invention contemplates that three or four finger prong elements may be spaced in any suitable configuration. For example, FIG. 3 depicts a preferred configuration wherein the finger prong elements 62a–c are spaced at approximately 60°, 120° and 270° respectively. An alternate finger prong spacing configuration is depicted in FIG. 6, wherein the finger prong elements 62a'–c' are spaced at approximately 90°, 225° and 315° respectively. As is apparent any suitable number of finger prong elements and spacing configuration is considered within the scope of the invention.

Each spine element 64 is fabricated and resiliently biased to form an arcuate shape when in an open position. In addition, the finger pong assembly 60 is selectively and incrementally movable from an open configuration wherein the finger prong elements 62a–c are substantially radially spaced as depicted in FIGS. 1 and 4, to a closed configuration wherein the finger prong elements 62a–c are substantially radially adjacent, by actuation of any suitable finger prong assembly closure mechanism. As previously discussed the finger prong assembly may be internally or externally biased to the open configuration when the finger prong elements are free from confinement, and may be moved to the closed configuration by either moving the slidable sleeve 48 forward, as shown in FIG. 2, thereby causing the finger prong elements to collapse within the confines of sleeve 48, or, as is discussed more fully herein below, by at least partially retracting the finger prong assembly into cannula 42 by actuation of movable handle 24.

As shown in FIGS. 3 and 5 for a first finger prong assembly configuration, and in FIGS. 8–10 for a second finger prong assembly configuration, movement of the finger prong assembly 60 to a closed position is facilitated by the internal structure of cannula 42. Specifically cannula 42 includes a prong actuating portion defined by the internal structure of the distal end 46 thereof. FIG. 5 depicts an embodiment of the distal end 46 of cannula 42 having a contoured inner wall structure 46a generally corresponding to the outer surfaces of the finger prong assembly 60 shown in FIG. 3. FIG. 9 depicts an alternate embodiment of the distal end 46' of alternate cannula 42 having a contoured inner wall structure 46a' corresponding to the finger prong assembly 60' shown in FIG. 6. As best shown in FIG. 10, the distal end 46' of cannula 42 may further include a distally diverging inner wall portion 46b' for facilitating the retraction thereby resulting in the closing of finger prong assembly 60'.

In FIGS. 11 through 14 there is shown a further alternate embodiment of the present invention, generally referenced as 100. The alternate embodiment surgical tool 100 includes a rigid handle housing, generally referenced as 200, which includes a first handle 220 rigidly attached to housing 200, and a second movable handle 240 pivotally attached to housing 200. In addition, there is a third movable handle 230 pivotally attached to housing 200. Movable handle 230 includes an end portion defining a pawl 231 for engaging ratchet-like teeth 241 on movable handle 240 for facilitating incremental adjustment and anchoring of movable handle 240 for reasons that will soon become apparent. Movable handle 240 is pivotally connected to handle housing 200 and further connected to a threaded end portion of shaft 500 by internally threaded connector 260. Helical spring 540 is disposed within handle housing 200 and biases shaft 500 toward an extended position relative to cannula distal end 460.

Figures 11, 17:
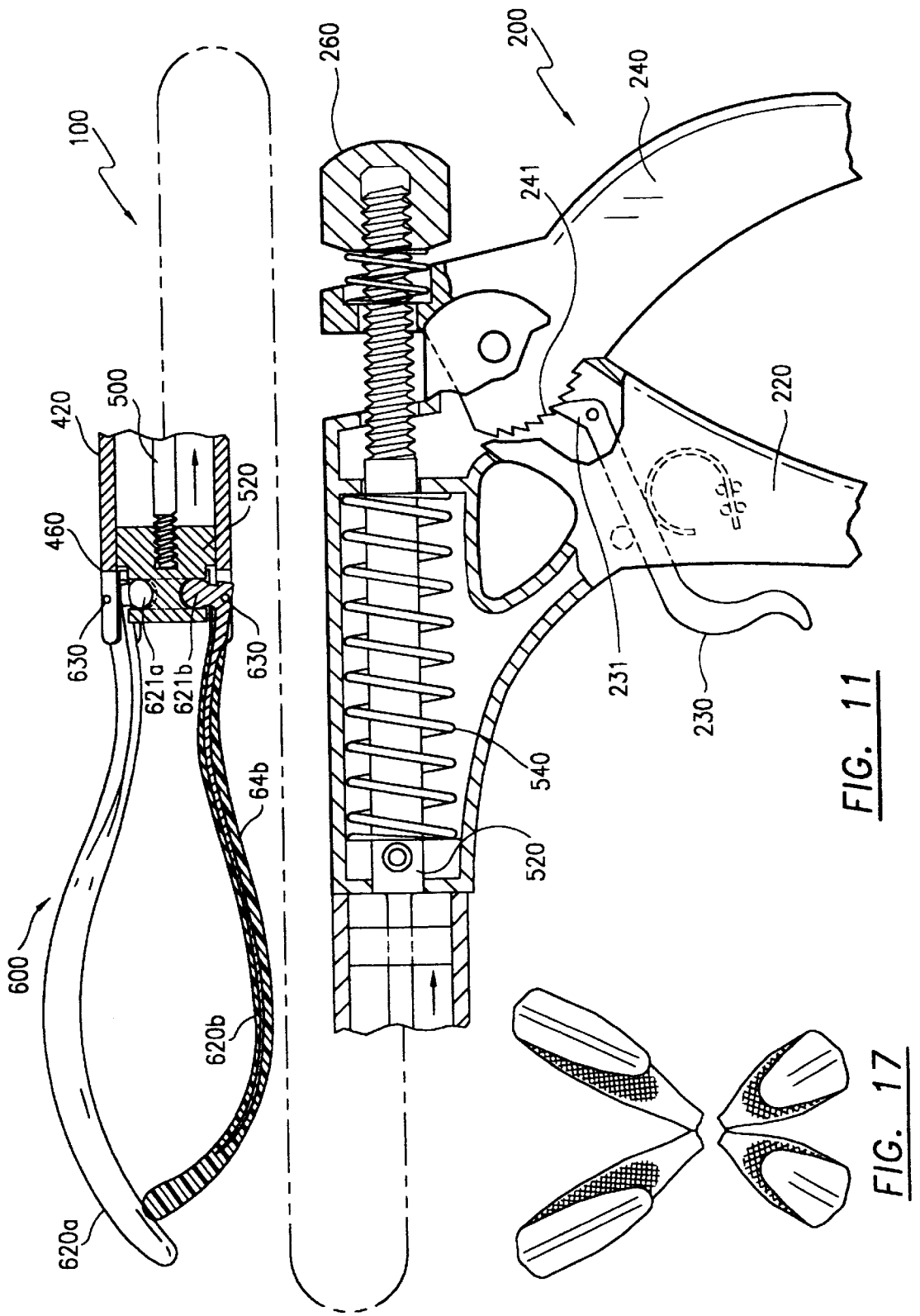
FIG. 11 is a fragmentary exploded side view of an alternate embodiment of the present invention in partial section.
FIG. 17 is a front elevational view depicting a four finger prong embodiment.
Figure 13:
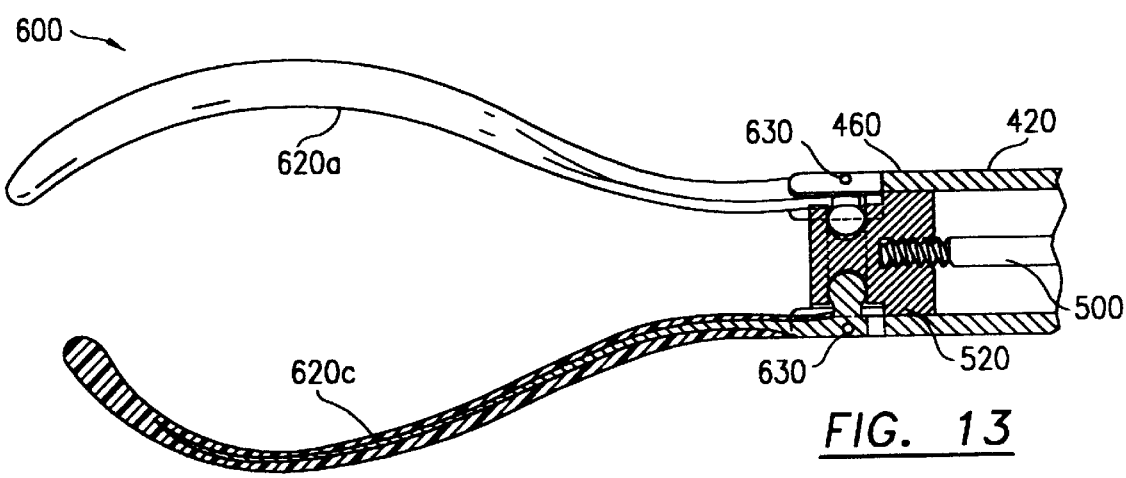
FIG. 13 is a fragmentary side sectional view taken along line 13—13 of FIG. 12.
Figure 12:
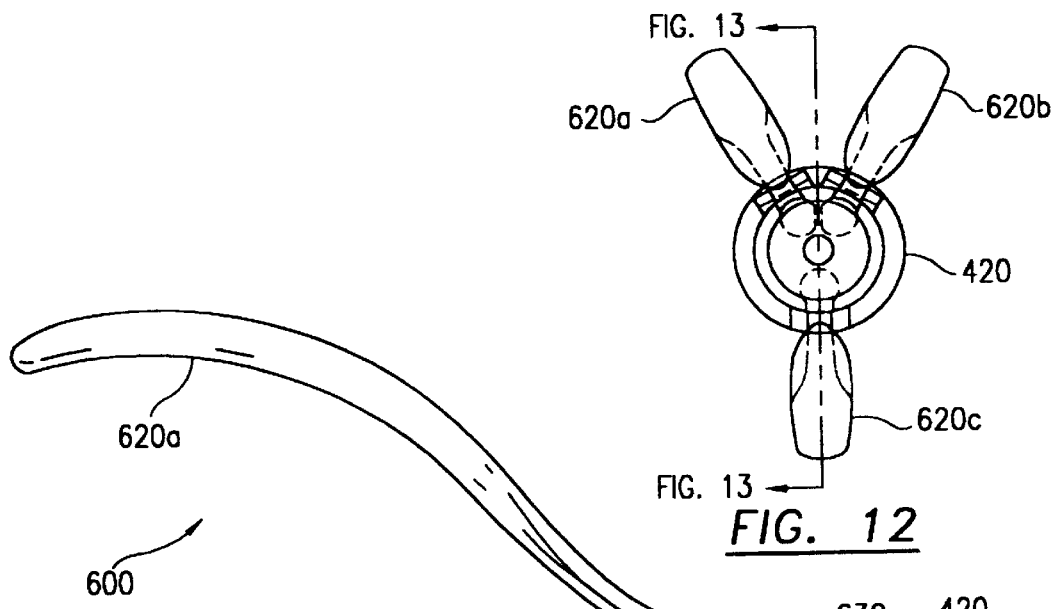
FIG. 12 is a partial front end view of the alternate embodiment of the finger prongs and prong actuating housing portion of the elongated cannula depicted in FIG. 11.
Figure 14:
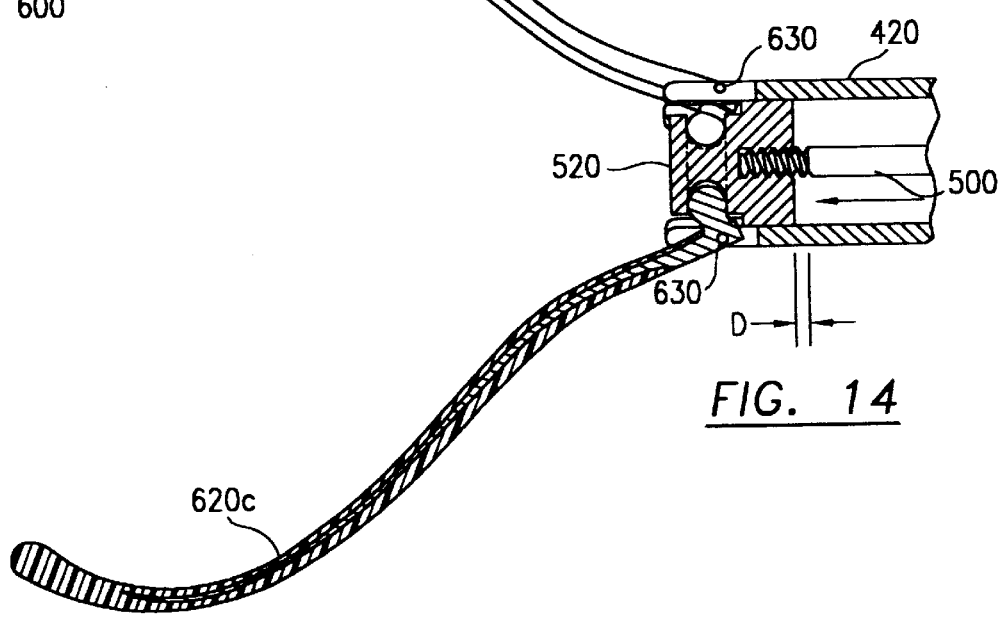
FIG. 14 is a side elevational view of the embodiment shown in FIG. 13, with the prongs in the open configuration.

As further depicted in FIG. 11, the alternate embodiment rigid actuating shaft 500 is connected at one end to movable handle 240 and connected at its opposite end to a finger prong assembly, generally referenced as 600, by a linkage mechanism 520. Actuation of movable handle 240 results in compression of spring 540 and the retraction of shaft 500 and finger prong assembly 600 relative to the distal end 460 of cannula 420. In this alternate embodiment, each finger prong element 620a–c is pivotally connected, via a pivot pin 630, to a portion of the distal end 460 of cannula 420. In addition, each finger prong element 620a–c includes a projecting ball portion, referenced as 621a–c respectively, matingly engaged with a socket receptacle defined by linkage mechanism 520. FIGS. 12–14 depict the finger prong assembly 600, wherein the finger prong assembly is shown in a closed configuration in FIG. 13., and an open configuration in FIG. 14. Specifically, FIG. 13 depicts linkage mechanism 520 in a retracted position corresponding to a closed finger prong assembly, while FIG. 14 depicts linkage mechanism 520 in an extended position, wherein shaft 500 has forced linkage mechanism to travel a distance, indicated as "D", from the retracted position depicted in FIG. 13, toward the distal end 460 of cannula 420 thereby causing partial rotation of each finger prong 620, about pivot pin 630, to an open configuration corresponding to an open finger prong assembly as shown in FIG. 14.

Figure 15:
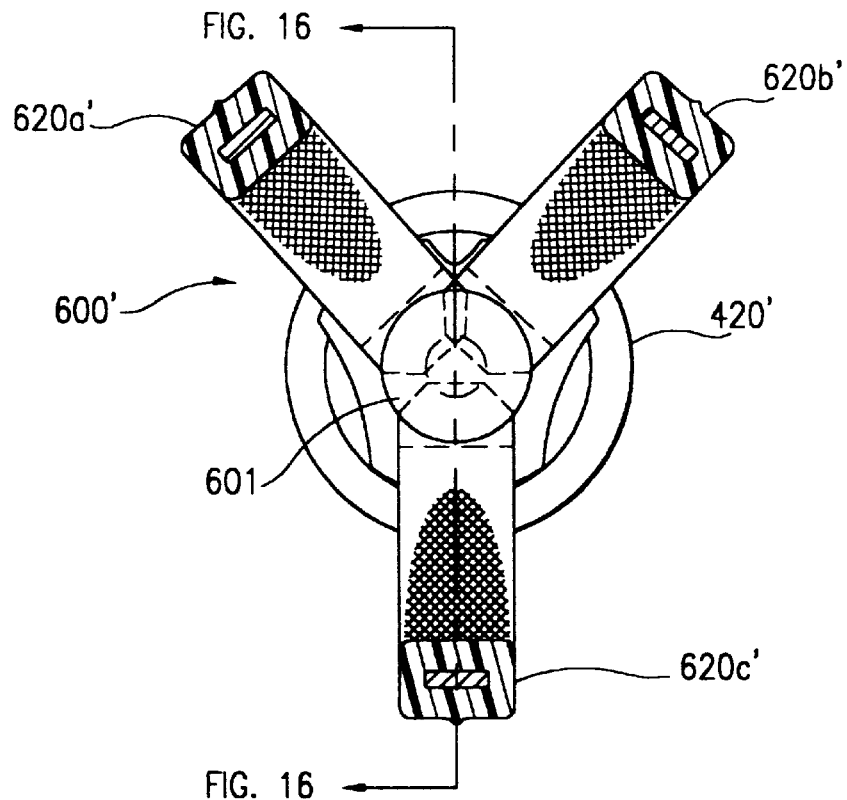
FIG. 15 is a front end elevational view of an alternate embodiment of the finger prongs and prong actuating housing.
Figure 16:
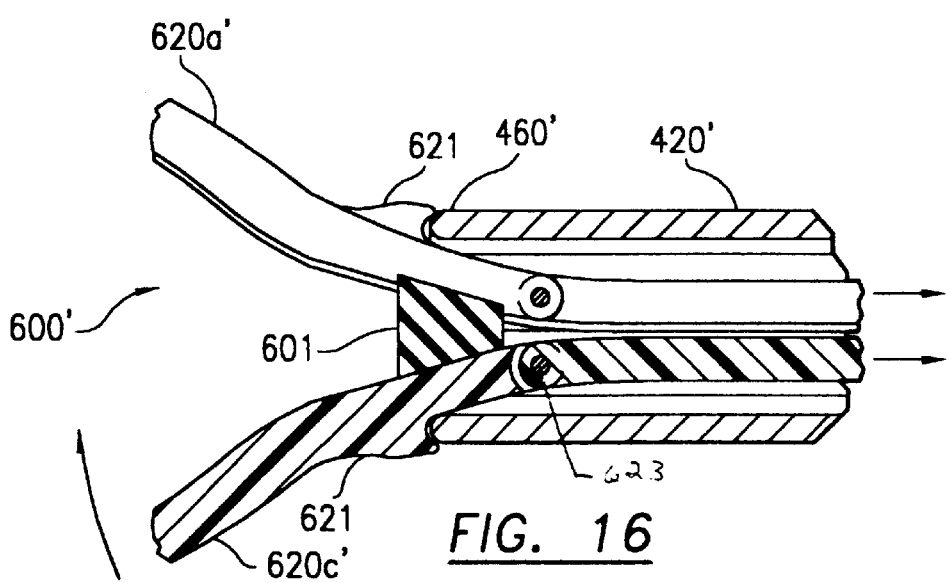
FIG. 16 is a fragmentary side sectional elevational view in partial section of an embodiment of the prong actuating housing portion of the elongated cannula, taken along line 16—16 of FIG. 15.

FIGS. 15 and 16 depict yet another alternate embodiment for facilitating the opening and closing of a the finger prong assembly. In this embodiment, the finger prong assembly 600' includes a resilient member 601 disposed between the three finger prong elements 620a'–c'. Resilient member 601 functions by producing a radially outward force on each finger prong element thereby biasing the finger prong assembly to an open configuration. The embodiment shown in FIGS. 15 and 16 further includes a projecting portion 621 on each finger prong element 620a'–c', and pivot connections 623. The projecting portions 621 each include a concave depression which functions by engaging the end 460' of cannula 420', during retraction of the finger prong assembly, thereby causing the finger prongs 620a'–c' to move radially inward toward the closed configuration as best depicted in FIG. 16.

With reference again to the preferred embodiment shown in FIGS. 1–5, the present invention is used during laparoscopic surgery to move, manipulate, anchor, or otherwise engage external portions of a body organ, such as the uterus, by first collapsing the finger prong assembly by moving slidable member 48 forward thereby collapsing the finger prongs 62 and inserting the cannula 42 into the patient through a laparoscopic trocar that has been inserted into the patient while simultaneously retracting slidable member 48 such that prongs 62 are collapsibly confined within the trocar. Upon exiting the distal end of the trocar, prongs 62 are biased to the open configuration whereby the prong members may be positioned proximate the exterior uterine wall. Next the prong members may be brought into engaging contact with the uterus by actuating movable handle 24 such that rigid actuating shaft 50 partially retracts the prong assembly into the distal end 46 of cannula 42 whereby the contoured inner wall structure 46a' guides the finger prongs 62 toward a closed position until the finger prongs sufficiently engage the outer uterine wall whereafter the user may manipulate the uterus as desired.

The present invention has been described specifically for use in the manipulation of the uterus during laparoscopic surgery. However, the present invention could also be used for laparoscopic surgery in which other solid organs such as the ovaries and the gall bladder or internal growths and fibrous tissues could be manipulated using the present invention. For such use it may be necessary to vary the size of the present invention for accommodating specific other body organs.

The instant invention has been shown and described herein in what is considered to be the most practical and preferred embodiment. It is recognized, however, that departures may be made therefrom within the scope of the invention and that obvious modifications will occur to a person skilled in the art. It should further be apparent that replacement of the mechanical components of the present invention with electrical or electronic components is a departure that is within the scope of the present invention.

What is claimed is:

1. A laparoscopic instrument for manipulating an internal organ during surgery, said instrument comprising:

cannula means sized for use with a surgical trocar;

finger prong means operatively associated with said cannula means, said finger prong means having a plurality of individually movable elongated finger prong elements, said finger prong elements being incrementally movable from an open configuration wherein said finger prong elements are substantially spaced, to a closed configuration wherein said finger prong elements are substantially adjacent;

grasping means connected to said cannula means;

actuating means, connected to said finger prong means, for incrementally moving said finger prong elements;

means for biasing said finger prong elements to said open position;

said means for biasing comprises a resilient spine included in each of said finger prong elements.

2. A laparoscopic instrument for manipulating an internal organ during surgery, said instrument comprising:

cannula means sized for use with a surgical trocar; finger prong means operatively associated with said cannula means, said finger prong means having a plurality of individually movable elongated finger prong elements, said finger prong elements being incrementally movable from an open configuration wherein said finger prong elements are substantially spaced, to a closed configuration wherein said finger prong elements are substantially adjacent;

grasping means connected to said cannula means;

actuating means, connected to said finger prong means, for incrementally moving said finger prong elements;

means for biasing said finger prong elements to said open configuration;

wherein said means for biasing includes a resilient member disposed between said finger prong elements.

3. A laparoscopic instrument for use with a surgical trocar for manipulating an internal organ during surgery, said instrument comprising:

an elongated cannula sized for insertion within a trocar;

finger prong means operatively associated with said cannula, said finger prong means having a plurality of individually movable elongated finger prong elements, said finger prong elements being incrementally movable from an open configuration wherein said finger prong elements are substantially spaced, to a closed configuration wherein said finger prong elements are substantially adjacent;

grasping means connected to said cannula means, said grasping means having a movable lever linked to said finger prong means for actuating said finger prong elements between said open and closed configurations; and wherein each of said finger prong elements includes a resilient spine surrounded by a protective coating.

4. A laparoscopic instrument according to claim 3, wherein said finger prongs define an elongated arcuate shape.

5. A laparoscopic instrument according to claim 3, further including a finger trigger linked to said finger prong means for incrementally actuating said finger prong elements between said open and closed configurations.

6. A laparoscopic instrument according to claim 5, wherein said finger trigger includes a ratchet linkage for facilitating incremental adjustment of said finger prong elements.

7. A laparoscopic instrument for use with a surgical trocar for manipulating an internal organ during surgery, said instrument comprising:

an elongated cannula sized for insertion within a trocar;

finger prong means operatively associated with said cannula, said finger prong means having a plurality of individually movable elongated finger prong elements, said finger prong elements being incrementally movable from an open configuration wherein said finger prong elements are substantially spaced, to a closed configuration wherein said finger prong elements are substantially adjacent;

grasping means connected to said cannula means, said grasping means having a movable lever linked to said finger prong means for actuating said finger prong elements between said open and closed configurations; and a tubular member disposed around said cannula means and slidably movable between an extended position wherein said finger prong elements are compactly confined within said slidable member, and a retracted position wherein said finger prong elements are free from confinement.

* * * * *